US005502129A

United States Patent [19]
Hergenrother et al.

[11] Patent Number: 5,502,129
[45] Date of Patent: Mar. 26, 1996

[54] TRIORGANOTIN LITHIUM, PROCESS TO PREPARE SAME AND ANIONIC POLYMERIZATION INITIATED THEREWITH

[75] Inventors: William L. Hergenrother, Akron, Ohio; W. Novis Smith, Philadelphia, Pa.; Anthony J. Muratore, III, Elverson, Pa.; Jay C. Sigle, Downingtown, Pa.; Mark T. Nemeth, Exton, Pa.

[73] Assignees: Bridgestone Corporation, Tokyo, Japan; Cyprus Foote Mineral Co., Malver, Pa.

[21] Appl. No.: 242,648

[22] Filed: May 13, 1994

[51] Int. Cl.$^6$ .................................. C08F 4/58; C07F 7/22
[52] U.S. Cl. ...................... 526/176; 526/173; 526/340; 556/82; 556/87; 260/665 R; 502/152
[58] Field of Search ...................................... 526/176, 190, 526/173; 556/82, 87; 210/767; 502/152; 260/665 R

[56] References Cited

U.S. PATENT DOCUMENTS

| | | |
|---|---|---|
| 3,177,190 | 4/1965 | Hsieh . |
| 3,317,918 | 5/1967 | Foster . |
| 3,393,182 | 7/1968 | Trepka . |
| 3,426,006 | 2/1969 | Nutzel et al. . |
| 3,439,049 | 4/1969 | Trepka . |
| 3,856,877 | 12/1974 | Otsuki et al. . |
| 4,015,061 | 3/1977 | Schulz et al. . |
| 4,026,865 | 5/1977 | Uraneck et al. . |
| 4,085,265 | 4/1978 | Otsuki et al. . |
| 4,247,418 | 1/1981 | Halasa et al. . |
| 4,278,781 | 7/1981 | Caspari et al. . |
| 4,414,372 | 11/1983 | Farnham et al. . |
| 4,429,091 | 1/1984 | Hall . |
| 4,476,240 | 10/1984 | Hall et al. . |
| 4,478,953 | 10/1984 | Yuki et al. . |
| 4,614,771 | 9/1986 | Watanabe et al. . |
| 4,616,069 | 10/1986 | Watanabe et al. . |
| 4,736,003 | 4/1988 | Schneider et al. . |
| 4,894,409 | 1/1990 | Shimada et al. . |
| 4,914,147 | 4/1990 | Mouri et al. . |
| 5,268,439 | 12/1993 | Hergenrother et al. . |

FOREIGN PATENT DOCUMENTS

| | | |
|---|---|---|
| 0067111 | 12/1982 | European Pat. Off. . |
| 0264506 | 4/1988 | European Pat. Off. . |
| 0282437 | 9/1988 | European Pat. Off. . |
| 0290883 | 11/1988 | European Pat. Off. . |
| 0316255 | 5/1989 | European Pat. Off. . |
| 138070 | 10/1979 | Germany . |
| 247455 | 7/1987 | Germany . |
| 0270713 | 8/1989 | Germany ................................ 556/87 |
| 2117778 | 10/1983 | United Kingdom . |

OTHER PUBLICATIONS

"An Improved Synthesis of p–Dimethylaminophenyl–Lithium" *Chemical Abstracts*, vol. 91, No. 12, Sep. 1979.
Chemical Abstracts, vol. 86, No. 10, Mar. 7, 1977, Columbus, Ohio, USA, T. AIKAWA "Pressure–sensitive Adhesives", p. 21, abstract–No. 55 967b & JP–A–76–125 473.
Chemical Abstracts, vol. 94, No. 6, Feb. 9, 1981, Columbus, Ohio, USA, B. I. Tarunin et al. "molecular complexes of trialkyltin chloride and chloro(dialkyl) tin hydroperoxide as initiators of vinyl monomer polymerization", p. 15, abstract–No. 31 282p & U.S.S.R.–A–763 349.
"Polymerization of Unsaturated Compounds in the Presence of Lithium Diethylamide" by Vinogradov et al, *Polymer Science USSR*, vol. 4, 1963.
"Preparation of Some Trialkyltin–lithium Compounds", J. Am. Chem. Soc., 75, 2507–2508 (1953) by Gillman and Rosenberg.
"New–Perfectly Difunctional Organolithium Initiators for Block Copolymers Synthesis: Synthesis of dilithium initiators in the absence of polar additives", Polymer, vol. 22, Dec. 1981, p. 1724, by Guyot, et al.
"Some Reactions of Tributyl–and Triphenyl–stannyl Derivatives of Alkali Metals", J. Chem. Soc., 1961, 618–622 by Blake, Coates, and Tate.
"The Organic Chemistry of Tin", interscience Publishers, 1971, by Wilhelm P. Neumann.
"Anionic Polymerization Initiators Containing Protected Functional Groups" Journal of Polymer Science, vol. 15, 1977, pp. 2401–2410, by Schulz et al.
"Anionic Polymerization Initiated by Diethylamide in Organic Solvents" by Angood et al. Journal of Polymer Science, vol. 11, p. 2777 (1973).
"Anionic Polymerization Initiators Containing Protected Functional Groups and Functionally Terminated Diene Polmers", Journal of Polymer Science, Polymer Chemistry Edition, vol. 12, pp. 153–166, by Schulz (1974).
"Anionic Polymerization" by Cheng, American Chemical Society Symposium Series 166, p. 513 (1981).

(List continued on next page.)

*Primary Examiner*—Fred Teskin
*Attorney, Agent, or Firm*—Hudak & Shunk Co.

[57] ABSTRACT

Solutions of triorganotin lithium are described having low residual concentrations (preferably less than 2,000 ppm) of halide. These are produced by a two-step process.

Triorganotin halide is reacted with lithium to produce hexaorgano ditin and a precipitate of lithium halide. The lithium halide precipitate is removed by filtration and/or use of highly concentrated reaction conditions. Then the hexaorgano ditin is further reacted with lithium to form the triorgano substituted tin lithium. The lithium halide is less soluble in hot tetrahydrofuran (THF) and/or more concentrated solutions. THF is a preferred solvent for the reaction. The low-temperature reactions described result in low amounts of inactive and/or undesirable byproducts. These triorganotin lithium compounds are useful as anionic initiators that result in polymers with terminal tin compounds, e.g., triorganotin, attached to the terminal end of the polymer where initiation occurred. The polymers with terminal tin compounds have lower hysteresis in cured carbon black-filled elastomeric compounds. Low concentrations of residual halides in the initiators and consequently in the polymers has been associated with reduced amounts of volatile organotin compounds being generated during processing of polymers with organotin terminal groups.

17 Claims, No Drawings

OTHER PUBLICATIONS

Kanga et al, "Makromolecules" 23, 1990, at pages 4235–4240.

Kanga et al, "Makromolecules" 23, 1990, at pp. 4241–4246.

"Preparation and Reactions of Trialkyltin", J. Org. Chem, 28, 237–239 (1963), by Tamborski, Ford and Soloski.

"A Bifunctional Anionic initiator Soluble in Non-Polar Solvents", Makromol. Chem. 179, 1978, pp. 551–555, by Beinert, et al.

"Bifunctional Anionic Initiators: A Critical Study and Overview", Makromol. Chem. 1986, 1985, pp. 2017–2024, by Bandermann, et al.

"Specific Functionalization of Polymers by Carboxyl Groups", Makromol. Chem. 179, 1978, pp. 1383–1386, by Broze, et al.

"3–Dimethylaminopropyl–Lithium—An Analytical and Kinetic Investigation of a New Initiator System for polymer Synthesis, European Polymer Journal", vol. 11, 1975, pp. 699–704, by Eisenbach, et al.

An article entitled "Preparation and Reactions of Trialkyltinlithium," C. Tamborski, F. Ford, and E. Soloski, *Journal of Organic Chemistry*, 1963, vol. 28, pp. 237–239.

"Synthesis of Organolithium Compounds of Some Group IV and V Elements", J. Org. Chem., 27, 619–621 (1962), by Tamborski, et al.

TRIORGANOTIN LITHIUM, PROCESS TO
PREPARE SAME AND ANIONIC
POLYMERIZATION INITIATED
THEREWITH

FIELD OF INVENTION

A triorgano substituted-tin lithium solution having low residual lithium halide content made by a two step process is disclosed. The organotin lithium can be used to initiate the polymerization of anionically initiated elastomers such as polydienes and copolymers of dienes and vinyl aromatic monomers. The polymers initiated with this initiator have triorgano substituted-tin end groups which react with carbon black fillers. This reaction results in cured carbon black filled elastomers with lower hysteresis, higher rebound, and less heat build-up than in similar polymers made with butyl lithium initiators.

BACKGROUND

U.S. Pat. No. 3,426,006 discloses tin containing organometal initiators made by reactions from 1 mole of stannous chloride with 3 moles of alkyl lithium (column 5, lines 29–38). These initiators are then used to form colorless polymers. This initiator type has been shown by Tamborski et al., *Journal of Organic Chemistry*, Vol. 28, page 237 (1963) to be predominantly an equilibrium mixture of dibutyltin and butyl lithium wherein the butyl lithium is the more active initiator and hence, only of a few of the polymer chains produced from its initiation actually contain tin atoms.

U.S. patent application Ser. No. 07/636,961 filed Jun. 2, 1991, which is published European Application 493839 of Jul. 8, 1992, discloses several alternate ways to make triorgano substituted-tin lithium initiators and their use to make organotin terminated polymers with reduced hysteresis. The initiators disclosed therein had higher residual ionic chloride concentration than claimed herein or were made with a more expensive distillation process which results in undesirable tetrabutyltin and/or tributyltin hydride impurities.

SUMMARY OF THE INVENTION

It has been found that a two-step process can convert triorgano substituted-tin halides to triorgano substituted-tin lithium in high yields and can substantially reduce unwanted lithium halide contaminant levels in the final solution of triorgano substituted-tin lithium. The two step process involves the reaction of the triorgano substituted-tin halide with lithium using a slight mole excess of lithium creating a hexaorgano substituted-ditin compound. The insoluble lithium halide produced in this reaction can be removed by filtration, preferably hot. LiCl is less soluble in warmer tetrahydrofuran (THF) solutions of the reaction product. Other steps to minimize residual lithium chloride contamination levels include using minimal amounts of solvating solvents such as tetrahydrofuran (THF) relative to the triorgano substituted-tin halide. For example the THF is desirably 35–80 wt. % of the concentrated product in solution prior to filtration. Alkane-type solvents are desirably used to wash the filtrate free of hexaorgano ditin and residual THF since these solvents do not carry LiCl contamination forward into step 2. Subsequently, the hexaorgano substituted-ditin compound can be reacted with additional lithium metal to produce a triorgano substituted-tin lithium compound having reduced amounts of lithium halides.

These triorgano substituted-tin lithium compounds can be used as initiators to make elastomers with one or more trialkyltin functionalized ends. These polymers with tin functionalized ends can be formulated with carbon black into rubber products having reduced hysteresis.

The triorgano substituted-tin lithium initiators with low residual halide concentrations made by this process also have low levels of organotin by-products such as tetrabutyltin. Polymers initiated with triorgano-substituted-tin lithium having high residual chloride, e.g. lithium chloride, levels are known to produce organotin chlorides during processing and compounding. These tetrabutyltins and organotin chlorides are volatile. The volatile organotin compounds are objectionable in the work place and are regulated and limited by the Occupational Safety and Health Act (OSHA).

The two-step process offers an economically viable way to make triorgano substituted-tin lithium initiators with good activity and low residual halide concentrations.

DETAILED DESCRIPTION OF THE INVENTION

The present invention produces a solution of triorgano substituted-tin lithium ($R_3SnLi$) in a pure form at approximately 10–55 wt. % active initiator with less than about 3,500, desirably less than 3000; preferably less than 2500 or 2000, more preferably from 100 or 200 to less than 1500 ppm of halide ions (such as $Cl^-$) based on the active organo substituted-tin lithium. The chloride content can be measured by ion chromatography. The residual lithium halide concentration from prior art disclosures of tin lithium initiators made from triorgano substituted-tin chloride averages more than 4,000 ppm $Cl^-$ based on the active organotin. Desirably the triorgano substituted lithium or the hexaorgano ditin have low levels of tetraorganotin (e.g., less than 20, 15, 10, or 5% by wt. based on the active initiator wt.) and low levels of triorganotin hydride (e.g., less than 10, 6.0, or 4.0 by wt. based on the active initiator wt.). Desirably the $R_3SnLi$ species are 90 or 93 wt. % or more of all tin containing species present in the initiator. These tin lithium compounds are useful as anionic initiators that result in polymer (elastomer) chains where at least one terminal chain end (the terminus where the initiation of polymerization occurred) has a triorgano substituted-tin group ($R_3Sn$)—. When the tin lithium disassociates to start polymerization, the triorgano substituted-tin anion adds to the monomer unit to form a carbon anion while the lithium atom becomes the counter ion which associates with the growing chain end.

When there are lithium halides present in the tin lithium initiator, they can be carried along in the anionic polymerization and will be present in the polymer and subsequently in the compounded elastomer. Lithium halides, especially lithium chloride, can further react with the triorgano substituted tin terminated polymer and carbon black to produce the original triorganotin chloride which has an undesirable odor. Furthermore, the produced $R_3SnCl$, especially $Bu_3SnCl$, is an environmental concern during processing of the compounded polymer stocks. Similar results are anticipated with potassium or sodium instead of lithium metal. Varying amounts of sodium metal can be used with lithium.

The triorgano substituted-tin lithium compounds are made from the reaction of triorgano substituted-tin halides ($R_3SnX$) with lithium metal (or optionally with partial substitution with sodium metal) in solvents inert towards the lithium metal. Examples of particularly effective solvating or solubilizing solvents are tetrahydrofuran (THF); ethers such as dimethyl ether, diethyl to diamyl ether, tetramethylene ethylene diamine; glymes such as monoglyme, ethyl glyme, diglyme, ethyl diglyme, triglyme, butyl diglyme, tetraglyme; or other diethers. THF is a highly preferred solvating or solubilizing solvent. Other solvents such as alkanes of 5–20 carbon atoms (such as hexane) may be used as a diluent. These alkane solvents are particularly beneficial to rinse useful reactants from the LiCl filter cake. Because LiCl is very insoluble in alkanes this rinse solvent minimizes the amount of LiCl carried forward from filtration steps. It is estimated that the LiCl filter cake may retain 10–15 wt. % of the active hexaorgano ditin prior to rinsing. These alkane solvents are not solubilizing solvents in this specification. Desirably the triorgano substituted-tin lithium initiator solution is substantially free of mineral oil.

The organo groups (R) of the tri, tetra and hexaorgano species can independently be alkyls including cyclic alkyls having from 1 to 12 carbon atoms or aryls or alkyl substituted aryls having from 6 to 15 carbon atoms. More desirably, the organo groups can be alkyls having from 2 to 8 carbon atoms, and most desirably, the organo groups are butyl groups. The halides (X) can be chloride, iodide, or bromide, ($Cl^-$, $I^-$, $Br^-$) and are more desirably chloride.

The triorgano substituted-tin lithium (initiator) is desirably a solution. The concentration of the initiator can be from about 0.001% to about 58% desirably from about 10 to about 50 or 55%, and preferably from about 20 or 30 to about 50 or 55% by weight of the solution.

The process to produce triorgano substituted-tin lithium is desirably conducted in equipment inert to the lithium metal. Examples of suitable materials include polyethylene, polypropylene, stainless steel, and glass-lined materials. The reactions are desirably conducted under an atmosphere inert to lithium such as helium or argon gas, and preferably argon gas. Trace amounts of moisture from all components is minimized by drying procedures such as drying the THF over calcium hydride. The process to make triorganotin lithium is desirably conducted in two separate steps with a filtration step in between and optional further filtration after the last step.

First Step

In the first step, triorganotin chloride is reacted with a near stoichiometric amount of lithium metal to form a concentrated solution of hexaorgano ditin. It is desirable that the reaction proceed only to the hexaorgano ditin in the first step to facilitate removal of the $Cl^-$ ions. The molar ratio of lithium to the triorgano substituted-tin halide can be from about 1.0 to about 1.5, desirably from about 1.0 to about 1.20, and preferably from about 1.0 to about 1.10 in the first step. Only a trace of the triorganotin lithium is found when near stoichiometric amounts of lithium metal are added. Small amounts of Na in the lithium metal was found to increase the reaction rates. The lithium metal used may be excess or recycled lithium recovered from the second step. The solubilizing solvent is not essentially present during the first step to solubilize the reactants or the products but it is convenient to use it in small amounts and it may help keep the lithium metal surface clean and reactive. The mole ratio of the solubilizing solvent: triorganotin chloride desirably is up to 3 and more desirably is from 0.5 to 2.0 and preferably is from 0.8 to 1.5. The higher mole ratio of solubilizing solvent to tin chloride allow the solubilization of more LiCl. Therefore, it is desirable to keep the mole ratio of solvent to tin chloride low such as 3 or less to form hexaorgano substituted ditin in concentrated solutions with respect to the solubilizing solvent resulting in low concentrations of soluble LiCl.

The reaction temperature can vary widely depending upon the amount of time available for the reaction. The rate of addition of the lithium metal to the triorganotin chloride or vice versa is limited by the cooling capacity of the reactor. Desirable reaction temperatures are from about 0° to about 65° C., desirably 5° to 40° C., and preferably from about 5° to about 15° C. to minimize the occurrence of side reactions that may lower yields or result in other reaction products. Any triorganotin lithium formed is believed to react with additional triorganotin chloride to form hexaorgano ditin. The reaction desirably proceeds to 100% conversion of the triorganotin chloride producing hexaorgano substituted-ditin compounds ($R_3Sn-SnR_3$) in about 90 to 100% yield along with lithium chloride. The insoluble lithium chloride results in crystals whose size can be optimized for filtration ease. The ditin solution can be up to 70 or 80 wt. % solids and is filtered to remove the lithium halide by-product. Several washes with heptane or other hydrocarbons are used on the cake and the solvents are included in the product. The lithium halide may be recycled to recover the lithium.

The lithium halides (especially lithium chloride) were unexpectedly found to be less soluble in hot THF than cold THF. Thus, the amount of soluble halide can be limited by keeping the solvent temperature high immediately prior to and during filtration. Consequently, it is desirable to keep the ditin solution in THF from about 10° or 20° to 70° C. and preferably about 30° to 65° C. during the filtration to minimize the amount of soluble lithium halide carried forward into the second step of the reaction. The chloride:product ratios at this stage of the reaction are similar to the chloride:product ratios in the final product. The use of alkanes as partial replacement for the solubilizing solvents also minimizes the soluble LiCl.

Second Step

In the second step, the hexaorgano ditin which is typically present in concentrations up to 70 or 80 wt. % in the solution, is desirably added to a slurry of lithium metal in additional solvating solvent (preferably THF). This order of addition minimizes side reactions of the hexaorgano ditin. Total addition and reaction times desirably vary from 5 to 16 hours depending on the particular equipment and its limitations. Longer times tend to result in more undesired by products. This gives a concentration desirably of from about 10 to 50 wt %, more desirably about 20 to 40 wt. % of active final product. Two moles of lithium react with one mole of hexaorgano ditin to form 2 moles of triorganotin lithium. An excess of from 10 to 105% of lithium helps to speed the reaction of hexaorgano ditin with lithium. The mole ratio of lithium to the ditin is desirably from about 2 to 6, more desirably from about 2.0 to 5.0, and preferably from about 2.0 to about 4.2. A Gilman titration can be used to determine the amount of active lithium present in the final product.

Desirable reaction temperatures are from about 0° to about 65° C., more desirably from about 5° to about 40° C. still more desirably from about 5 to about 25, and preferably from about 10° to about 15° C. Lower temperatures during this reaction have been found to minimize the formation of organotin by-products such as tetrabutyltin and tributyltin hydride. The reaction product may be filtered to remove the unreacted lithium metal which can be used for a subsequent batch in the first step. The filtrate is a triorgano substituted-tin lithium initiator. The filter cake is rinsed with hydrocarbon solvent or solubilizing solvent and the rinse is optionally combined with product. The mole ratio of solubilizing solvent to organo substituted-tin lithium in this step and the final product is desirably 3 or more and more desirably 3 to 6. These ratios are desirable in that they are sufficient to solubilize the tin species but are not unnecessarily dilute.

The triorganotin lithium has utility for initiating the anionic polymerization of monomers capable of anionic polymerization. The triorganotin lithium is also useful as an intermediate in the synthesis of other compounds, particularly in the synthesis of pharmaceutical products. The monomers include compounds having at least one carbon-carbon double bond which is capable of polymerization through the double bond. Other monomers can include cyclic ethers and lactones that polymerize through ring opening reactions. Suitable monomers include dienes having from 4 to 12 carbon atoms (preferably conjugated dienes), monovinyl aromatic monomers having from 8 to 18 carbon atoms and trienes. In copolymers of dienes and monovinyl aromatics, the weight ratios of conjugated diene to aromatic vinyl monomers are desirably from 95–50:5–50, preferably 95–55:5–45.

These triorgano substituted-tin lithium compounds can be used as initiators to make elastomeric polymers with one or more trialkyltin functionalized ends. These polymers with tin functionalized ends can be formulated with carbon black in elastomeric products with reduced hysteresis.

One source of increased hysteresis in elastomers during flexing is the section of the polymer chain from the last crosslink of the vulcanizate to the end of the polymer chain. The free polymer chain end cannot elastically store energy. As a result, the energy transferred to this polymer chain end is lost as heat. One method to reduce this type of hysteresis energy loss is to create a polymer chain end with terminal tin groups. Tin has an affinity for carbon black reinforcing fillers and chemically reacts with the quinone functionality present on carbon black. This reaction of the tin-terminated polymer chain end with carbon black is believed to reduce hysteresis. This is further explained in an article in Rubber Chemistry and Technology, 1990, vol. 63, no. 1, by F. Tsutsumi et al. entitled "Structure and Dynamic Properties of Solution SBR Coupled with Tin Compounds" pp 8–22 which is hereby incorporated by reference. Cured carbon black filled polymer compositions are useful in many applications requiring low heat buildup during flexing. One such application is in tires where rolling resistance is reduced due to lower hysteresis.

Polymerizations using these initiators are usually conducted in conventional hydrocarbon solvents for anionic polymerizations such as hexane, cyclohexane, benzene and the like. A polymerization terminating agent can be used to functionalize the chain end where termination occurs. Active terminating agents include compounds having abstractable hydrogen atoms such as water or alcohol. The growing chain ends can be functionalized or coupled to other species with compounds providing terminal functionality. These include tin tetrachloride, $R_3SnCl$, $R_2SnCl_2$, $RSnCl_3$, carbodiimides, N-methylpyrolidine, cyclic amides, cyclic ureas, isocyanates, Schiff bases, 4,4'-bis(diethyl amino) benzophenone, and other functionalizing agents well known to the art, wherein each R group is individually alkyls having from 1 to 20 carbon atoms, cycloalkyls having from 3 to 20 carbon atoms, aryls having 6 to 20 carbon atoms, or aralkyls having 7 to 20 carbon atoms.

Preferred terminating or coupling agents for this application are various tin alkoxides of the formula $R_xSn(OR)_{4-x}$ where x is from 0 to 3 and each R group can be the organo group described above and preferably the R groups are limited to lower alkyls (i.e., 1 to 8 carbon atoms). These tin containing compounds are preferred in that they help minimize the amount of chloride contaminants retained by the polymer. As previously explained, the chloride contaminants contribute to the production of volatile organotin by-products from the organotin terminated polymers.

Anionic polymerizations using the triorgano substituted-tin lithium initiators can be conducted according to polymerization techniques well known to the art. The mole ratio of initiator to monomers limits the molecular weight in the absence of chain transfer or chain termination reactions. The monomer can be added batchwise or incrementally. Lower polymerization temperatures tend to minimize chain transfer and termination reactions. Polar coordinators may be added to control the vinyl content in diene polymerizations or to aid in randomization in copolymerizations. Amounts of polar coordinators may range from 0.001 to 90 or more equivalents per equivalent of lithium.

Compounds useful as polar coordinators include tetrahydrofuran, linear and cyclic oligomeric oxolanyl alkanes such as 2,2'-di(tetrahydrofuryl) propane, dipiperidyl ethane, hexamethylphosphoramide, N,N'-dimethylpiperazane, diazabicyclooctane, dimethyl ether, diethyl ether, tributylamine and the like. The linear and cyclic oligomeric oxolanyl alkane modifiers are described in U.S. Pat. No. 4,429,091, which is hereby incorporated by reference. Other polar coordinators include compounds having an oxygen or nitrogen heteroatom and a non-bonded pair of electrons. Examples include dialkyl ethers of mono and oligo alkylene glycols; "crown" ethers; tertiary amines such as tetramethylene diamine (TMEDA); tetrahydrofuran (THF), THF oligomers, alkylated versions of THF and the like.

The polymers produced with the triorganotin lithium initiator of this invention as the sole initiator will have essentially one or more organo substituted-tin group per polymer chain with said essentially one group being derived from the initiator. If an organo substituted-tin terminating agent or a coupling agent is used, the molar ratio of triorganotin to polymer chains can be above 1.60:1, desirably above 1.80:1, and preferably above 1.95:1. The triorganotin compound ($R_3Sn$—) is the first unit of the polymer chains initiated by these initiators. The growing polymer chain thus has the structure $R_3Sn$—(repeat unit)—Li+. The growing anionic chain end can then be functionalized as described above. The residual halogen in the polymer is less than 3500 ppm; and preferably less than about 2500 or 2,000 ppm; and more preferably from about 100 or 200 to 1500 ppm based on the wt. of the triorganotin groups due to the low concentration of residual halogen, desirably $Cl^-$, in the initiator of this invention.

The triorgano substituted-tin lithium initiators of this invention are very stable to loss of initiator activity with storage. Butyl lithium stored in THF in a sealed glass ampule loses activity as an initiator during storage. The triorganotin lithium initiators dissolved in THF and stored in glass ampules at temperatures from 20° C. up to 35° C. maintain their activity without measurable losses for periods of six months or more.

The triorgano substituted-tin compounds of this invention have low amounts of organotin by-products due to the mild reaction conditions used, such as low temperatures. One example of such effect is that the initial tributyl substituted-tin lithium produced had from 8 to 10 mole % tetrabutyltin as a contaminant in the product. This contaminant contributes to the volatile organotin in the air and doesn't function as an initiator. By controlling the reaction conditions, tributyl substituted-tin lithium samples can be made having only 2 or 3 mole percent of tin in the tetrabutyl tin form. It is anticipated that distilling the hexaorgano ditin would result in substantial amounts of tetrabutyltin relative to the hexaorgano ditin made in the first step. The polymers initiated with the triorganotin lithium initiators find use in compounded rubber stocks. The organotin groups on the ends of the polymer can chemically react with function groups such as quinones on the carbon black used in many rubber stocks. This chemical reaction between the polymer chain ends and the carbon black reduces hysteresis in the cured rubber stock. In applications such as tire where there is a constant flexing of the rubber, this can reduce rolling resistance and minimize heat buildup.

EXAMPLE 1

The above process may be better understood by the following example. 6.89 kg of tri-n-butyltin chloride was reacted in 1.8 kg of tetrahydrofuran (THF) with 0.187 kg of lithium metal. A finely divided or powdered lithium metal reacts more quickly than large solid portions. This reaction takes about 2 hr. with stirring at 15°–35° C. The insoluble lithium halide in the reaction product (present as a precipitate) is removed by hot filtration, e.g. 55° C. from the solution of hexa-n-butyl-ditin in THF. The LiCl can be washed free of tin (Sn) compounds with pentane or heptane and then recycled to recover the Li. The filtered solution of hexa-n-butyl-ditin is gradually added to a reactor containing enough THF (about 3.6kg) to have a 3:1 mole ratio of solvent to triorganotin lithium and 0.35 kg of lithium metal. This reacts for about 4 hours at a temperature of 25°–50° C. to form a solution of lithium tri-n-butyl tin in THF. This is filtered again to remove any excess lithium metal present and any non-soluble tin containing by-products.

EXAMPLE 2

First Step

A stirred tank reactor is purged with argon charged with 13 pounds (1.87 lb-moles) lithium metal dispersion and 170 lbs (2.36 lb-moles) tetrahydrofuran (THF). (The lithium metal contained 0.5% sodium metal.) The lithium metal dispersion may either be a fresh charge or the excess metal filtered from the second reaction step and recycled to the first step. The stirred slurry is maintained at 10°–15° C. while 570 pounds of tri-n-butyltin chloride (1.75 lb-moles) is added over a period of 8–10 hours. The reaction is noticeably exothermic and proceeds rapidly. (The rate of addition is a function of the cooling capacity of the reactor.) After the addition is completed, the reaction mass is stirred an additional hour before allowing the temperature to rise to room temperature over a two hour period. It may then be filtered.

The reaction slurry is then filtered to remove the lithium chloride which formed in the reaction. The filter cake is washed twice with heptane to remove the residual hexabutyl ditin and THF. These washings are combined with the THF filtrate containing hexabutyl ditin to provide the feed for the second step reaction. The yield to the hexabutyl ditin product is about 85 to 95%. The chloride content of the solution is less than 2000 ppm with a hexabutyl ditin concentration of about 70–80% by weight.

Second Step

A stirred tank reactor is purged with argon and charged with 22 pounds of lithium metal (0.5% wt. sodium) and 334 pounds of THF. The stirred slurry is cooled to 5°–15° C. and maintained at this temperature while the combined filtrate from the first step is added over 6–8 hours. The reaction is mildly exothermic during the first half of the reaction. The reaction slurry is stirred an additional four hours after the addition is complete at 10°–15° C. The reaction slurry is then allowed to warm up to ambient temperature over two hours and then stirred several additional hours. The product slurry is then filtered and the filter cake washed with heptane which is combined with the product solution. The final product solution contains about 30–35% lithium tri-n-butyl-tin at an overall yield of 76–80%. The filter cake consisting primarily of lithium metal can be recycled to be the lithium charge for step one.

EXAMPLE 3

Since there is a concern about the volatile organotin compounds that may be generated during compounding and curing of the polymers made using triorgano substituted-tin lithium initiator, an experiment was set up to determine the effect of $Cl^-$ in a tributyl substituted-tin lithium (TBTL) on the amount of extractable $Bu_3SnCl$ in a cured rubber sample. The experimental procedure is described below and the data is summarized in Table I.

To a 2 gal. (7.6 l) stainless steel reactor was added 2.02 lbs. (916 g) of 33% styrene in hexane and 7.00 lbs. (3.18 kg) of 24.5% butadiene in hexane. After cooling to 55° F. (13° C.) from 1.0 to 1.5 millimoles of 2,2'-ditetrahydrofuryl propane and 8.7 to 10.9 millimoles of an approximately 50 wt. % tributyltin lithium (TBTL) in THF were added. The temperature was held at 55° F. (13° C.) for 1.5 hrs. before increasing to 70° F. (21° C.) and then every 5 minutes increasing another 10° F. (5.6° C.) until 120° F. (49° C.) was reached. A 4.0 lbs. (1.8 kg) sample was removed and terminated with isopropyl alcohol and dibutyl para-cresol (DBPC) was added an antioxidant. The polymer was analyzed for its $ML_4$ @ 212° F. (100° C.), % styrene, % vinyl PBD and Tg which are listed in the attached Table I.

TABLE I

| Polymer Sample # | ppm $Cl^-$ in TBTL initiator | $Bu_3SnAm$ ppm | $ML_4$ 100° C. | Styrene % | PBD % V | Tg (°C.) |
| --- | --- | --- | --- | --- | --- | --- |
| 1 | 6325 | 819 | 57.4 | 20.7 | 61.2 | −36.2 |
| 2 | 3770 | 450 | 10.3 | 21.8 | 78.4 | −18.8 |
| 3 | 2425 | 466 | 27.3 | 28.4 | 57.9 | −29.9 |
| 4 | 2425 | 645 | 9.4 | 30.7 | 55.8 | −31.3 |
| 5 | 830 | 90.1 | 78.4 | 27.4 | 63.4 | −21.4 |
| 6 | 830 | 128 | 23.6 | 30.1 | 55.7 | −24.1 |
| 7 | 830 | 185 | 26.9 | 31.1 | 56.4 | −23.2 |
| 8 | 40 | 55.0 | 30.5 | 30.0 | 56.0 | −26.3 |
| 9 | 40 | 114 | 16.2 | 29.2 | 56.0 | −26.4 |
| 10 | 40 | 55.4 | 82.2 | 29.5 | 54.5 | −26.6 |

Test plaques were produced by compounding 100 parts of this rubber in a Brabender with 50 phr carbon black, 3 phr zinc oxide, 1 phr antioxidant, 1–8 phr sulfur, 2 phr stearic acid, and 1 phr of accelerator and then curing for 30 min. at 300° F. (149° C.). Extraction with hexane, treatment of the extract with amyl magnesium bromide (AmMgBr) and analysis by GC using a flame photometric detector and a tetrapropyltin ($Pr_4Sn$) internal standard allowed the determination of extractable tributyltin chloride ($Bu_3SnCl$) measured as Bu3SnAm. Table I shows lower concentrations of Bu₃SnCl were formed when the concentration of Cl⁻ was less than 2000 ppm based on the weight of the initiator.

While in accordance with the Patent Statutes, the best mode and preferred embodiment has been set forth, the scope of the invention is not limited thereto, but rather by the scope of the attached claims.

What is claimed is:

1. A triorgano substituted-tin lithium initiator, comprising; the reaction product of a solution of hexaorgano substituted-ditin with lithium metal in the presence of one or more solubilizing solvents which form the triorgano substituted-tin lithium, said reaction product having less than 3000 parts of a halide based on one million parts of said triorgano substituted-tin lithium initiator and said reaction product having at least 90 percent by weight of said triorgano substituted-tin lithium based on all of the tin containing species in said reaction product, wherein the mole ratio of said solubilizing solvents to said triorgano substituted-tin lithium is above 3:1, and wherein said organo groups are independently an alkyl or a cyclo-alkyl having from 1 to 12 carbon atoms or an aryl or an alkyl substituted aryl having from 6 to 15 carbon atoms.

2. A triorgano substituted-tin lithium initiator according to claim 1, wherein the halide is chloride and its concentration is less than 2000 ppm based upon said triorgano substituted-tin lithium, and wherein said organo groups are independently an alkyl of 3–4 carbon atoms and wherein said one or more solubilizing solvents comprise tetrahydrofuran.

3. A triorgano substituted-tin lithium initiator according to claim 2, having a halide concentration of from 100 to 1500 ppm based upon said triorgano substituted-tin lithium.

4. A triorgano substituted-tin lithium initiator according to claim 2, wherein said organo groups are butyl groups and wherein said tributyltin lithium is 93 wt. % or more of all tin containing species in said reaction product, and wherein said reaction is carried out at a temperature of less than 40° C.

5. A triorgano substituted-tin lithium according to claim 2, wherein said organo groups are butyl groups.

6. A process for producing a solution of triorgano substituted-tin lithium comprising the steps of:
reacting a triorgano substituted-tin halide with lithium metal in the presence of a solvent having one or more solubilizing solvents with a mole ratio of said one or more solubilizing solvents to said triorgano substituted-tin halide of less than 3:1 and forming a solution of hexaorgano substituted-ditin and lithium halide precipitate,
removing said lithium halide precipitate from said solution of hexaorgano substituted ditin, and
reacting said hexaorgano substituted-ditin with lithium metal and adding one or more solubilizing solvents which can be the same and/or different than said one or more solubilizing solvents of said triorgano substituted-tin halide step, and forming the triorgano substituted-tin lithium with the mole ratio of the total amount of said one or more solubilizing solvents to the triorgano substituted-tin lithium being 3 or greater,
wherein said organo groups are independently an alkyl or a cycloalkyl having from 1 to 12 carbon atoms or an aryl or an alkyl substituted aryl having from 6 to 16 carbon atoms.

7. A process for producing a solution of triorgano substituted-tin lithium according to claim 6, wherein said one or more solubilizing solvents of said solution comprise tetrahydrofuran.

8. A process for producing a solution of triorgano substituted-tin lithium according to claim 7, wherein said triorgano substituted-tin lithium solution has a halide concentration of from 100 to 1500 parts based on one million parts of said triorgano substituted-tin lithium, and wherein said lithium halide precipitate is removed by filtration.

9. A process for producing a solution of triorgano substituted-tin lithium according to claim 8, wherein said halide is chloride and said organo groups are butyl, and wherein said reaction product contains at least 90 percent by weight of triorgano substituted-tin lithium based on all of the tin containing species in the solution.

10. A process for producing a solution of triorgano substituted-tin lithium according to claim 9, further including filtering said triorgano substituted-tin lithium to remove unreacted lithium and insoluble tin compounds.

11. The reaction product of claim 6.

12. The reaction product of claim 10.

13. A process for producing a solution of hexaorgano substituted-ditin comprising:
combining in the presence of a solvent a triorgano substituted-tin halide with an effective amount of lithium metal to form a solution primarily of hexaorgano substituted-ditin and lithium halide, said solvent being one or more solubilizing solvents in an amount such that the mole ratio of said solubilizing solvents to the triorgano substituted-tin halide is 3.0 or less, and
separating the lithium halide which precipitates from the hexaorgano substituted-ditin,
wherein the resulting hexaorgano substituted-ditin solution has less than 3000 parts of halide per million parts of said hexaorgano substituted-ditin.

14. A process according to claim 13, wherein said one or more solubilizing solvents comprise tetrahydrofuran and the organo groups of said hexaorgano substituted-ditin independently is an alkyl or a cycloalkyl of from 1 to 12 carbon atoms, and wherein said resulting hexaorgano substituted-ditin solution has a halide concentration of less than 2000 ppm.

15. A process according to claim 13, wherein said organo groups are butyl.

16. A process for anionically polymerizing one or more monomers into a polymer with reduced hysteresis and low levels of volatile organotin by-products when said polymer is compounded in carbon black-filled elastomers, said process comprising:
reacting a triorgano substituted-tin lithium initiator solution with at least one diene monomer and optionally a monovinyl aromatic monomer to form a polymer with triorgano substituted-tin groups on at least one end, wherein said initiator solution has a residual halide content of less than 3000 parts based on one million parts of said triorgano substituted-tin lithium initiator, wherein the amount of said triorgano substituted-tin lithium initiator is at least 90 percent by weight based on all of the tin containing species in said initiator, wherein said organo groups of said initiator independently is an alkyl or a cycloalkyl having from 1 to 12 carbon atoms or an aryl or an alkyl substituted aryl having from 6 to 15 carbon atoms, and wherein said diene has from 4 to 12 carbon atoms and wherein said monovinyl aromatic monomer has from 8 to 18 carbon atoms.

17. A process according to claim 16, wherein said organo groups of said initiator independently is an alkyl of 3 or 4 carbon atoms and wherein said initiator solution has a residual halide content of less than 2000 ppm.

* * * * *